US005141942A

United States Patent [19]
Lal et al.

[11] Patent Number: 5,141,942
[45] Date of Patent: Aug. 25, 1992

[54] PHARMACEUTICAL COMPOSITIONS COMPRISING LABDANE DITERPENOID DERIVATIVES AND PYRIMIDO(6,1-A)ISOQUINOLIN-4-ONE DERIVATIVES AND THEIR USE

[75] Inventors: Bansi Lal; Jürgen Blumbach; Alihussein N. Dohadwalla; Noel J. de Souza, all of Bombay, India

[73] Assignee: Hoechst Aktiengesellschaft, Frankfurt am Main, Fed. Rep. of Germany

[21] Appl. No.: 437,892

[22] Filed: Nov. 17, 1989

[30] Foreign Application Priority Data

Nov. 19, 1988 [EP] European Pat. Off. ........ 88119255.3

[51] Int. Cl.$^5$ ............................................. A61K 31/505
[52] U.S. Cl. ..................................... 514/267; 514/455
[58] Field of Search ................................ 514/267, 455

[56] References Cited

U.S. PATENT DOCUMENTS

| 4,088,659 | 5/1978 | Bhat et al. | 260/345.2 |
| 4,134,986 | 1/1979 | Bajwa et al. | 424/283 |
| 4,482,556 | 11/1984 | Lal et al. | 424/251 |
| 4,598,148 | 7/1986 | Lal et al. | 544/252 |
| 4,724,238 | 2/1988 | Dohadwalla et al. | 514/455 |

OTHER PUBLICATIONS

Chemical Abstracts 101:191834m (1984).
Chemical Abstracts 104:122398x (1986).

Primary Examiner—Leonard Schenkman
Attorney, Agent, or Firm—Finnegan, Henderson, Farabow, Garrett and Dunner

[57] ABSTRACT

Pharmaceutical compositions comprising labdane diterpenoid derivatives and pyrimido(6,1-a)-isoquinolin-4-one derivatives when administered to the skin of a mammal or of the man increase the rate of terminal hair growth, stimulate the conversion of vellus hair to growth as terminal hair and arrest hair loss. They can be used for the treatment of several kinds of alopecia.

2 Claims, No Drawings

PHARMACEUTICAL COMPOSITIONS COMPRISING LABDANE DITERPENOID DERIVATIVES AND PYRIMIDO(6,1-A)ISOQUINOLIN-4-ONE DERIVATIVES AND THEIR USE

The invention described herein relates to pharmaceutical compositions comprising at least one substance selected from the group of compounds named labdane diterpenoid derivatives and at least one substance selected from the group of pyrimido(6,1-a)isoquinoline-4-one derivatives.

Another aspect of the invention is the use of said pharmaceutical compositions for increasing the rate of terminal hair growth, for stimulating the conversion of vellus hair to growth as terminal hair and for arresting the loss of hair as potential methods for the treatment of alopecia.

Alopecia or Baldness is an affliction resulting from loss of hair. Different types of hair loss (alopecia areata, alopecia totalis, androgenetic alopecia) are recognised by dermatologists, the most common by far being known as androgenetic alopecia or male pattern alopecia or baldness. While this type of hair loss is largely confined to males, it is not unknown in women. The condition of alopecia or baldness is a consequence of a combination of factors:

(1) transition of hairs from terminal to vellus,
(2) increased number of telogen hairs—some of which have been shed, and
(3) loss of hair follicles.

Very little is known about the cause of male pattern baldness, although it is felt that it could be genetic or hormonal in origin. At the present time, the treatment of male pattern alopecia is attempted either through non-drug related approaches such as hair transplantation, ultra-violet radiation massage, psychiatric treatment and exercise therapy or through drug therapy. The non-drug related approaches to the problem are stated to be either generally ineffective or in the case of transplantation too costly, time-consuming and impractical. In the case of drug therapy, many types of therapeutic drugs ranging from vitamins to hormones, or diphenylhydantoin or streptomycin have been tried and only recently there has been an indication of moderate success. Among treatments which have shown some promise to have grown hair through topical application to the scalp of a human being suffering from male pattern baldness are the use of a microemulsion cream containing estradiol and oxandrolone or organic silicon or minoxidil.

Furthermore, the use of pyrimido(6,1-a)isoquinolin-4-one derivatives for the treatment of alopecia has already been proposed in the German patent application P 38 16 995.9.

Surprisingly, it has now been found that a pharmaceutical composition containing at least one diterpenoid derivative and at least one pyrimido(6,1-a)isoquinolin-4-one derivative is effective for increasing the rate of terminal hair growth, stimulating the conversion of vellus hair to growth as terminal hair and for arresting hair loss. Thus, said pharmaceutical composition is qualified for example for the treatment of alopecia, in particular for the treatment of the male pattern alopecia.

The instant invention relates to a pharmaceutical composition containing at least one compound of group A) consisting of labdane diterpeniods and at least one compound of group B) consisting of pyrimido(6,1-a)isoquinolin-4-one derivatives.

Labdane diterpeniod derivatives, for which a compound named Forskolin isolated from *Coleus forskolii* (Bhat, Bajura, Dornauer, de Souza, Fehlhaber, Tetrahedron Lett., 1669 (1977), Medicinal Research Reviews, Vol. 3, No. 2, 201-219 (1983)) is an example, are described in the following patents and patent applications:

| a) | Deutsche Offenlegungsschrift | 2 557 784 |
|---|---|---|
| | Deutsche Offenlegungsschrift | 2 654 796 |
| | Deutsche Offenlegungsschrift | 3 502 686 |
| | Deutsche Offenlegungsschrift | 3 502 685 |
| | Deutsche Offenlegungsschrift | 3 535 086 |
| | Deutsche Patentanmeldung | 37 18 589 |
| | Deutsche Patentanmeldung | 37 30 748 |
| | Indian Patent | 147 007 |
| | Indian Patent | 148 680 |
| | Indian Patent Application | 345/BOM/84 |
| | Indian Patent Application | 346/BOM/84 |
| | Indian Patent Application | 122/BOM/85 |
| | Indian Patent Application | 50/BOM/87 |
| | Indian Patent Application | 51/BOM/87 |
| | Indian Patent Application | 238/BOM/87 |
| | Indian Patent Application | 265/BOM/87 |
| | Indian Patent Application | 266/BOM/87 |

The compounds, in particular the compounds of the examples of said patents patent applications are preferred compounds of group A) of the instant application.

Further preferred compounds of group A) are selected from the compounds characterized by formula I

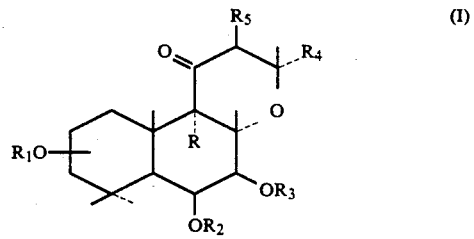

wherein R denotes H, OH, O-$(C_1-C_3)$-alkyl or

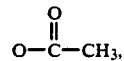

$R_1-R_3$ denote independently from each other H, $(C_1-C_6)$-alkyl, $(C_1-C_6)$-alkenyl, $(C_1-C_6)$-alkynyl, $(C_3-C_8)$-cycloalkyl, dialkylamino or aralkyl in which the alkyl groups have at most 4 carbon atoms, $(C_1-C_{20})$-acyl, $(C_2-C_{10})$-alkoxycarbonyl, $(C_2-C_{10})$-arylaminocarbonyl or either all three or only two or one of the substituents $R_1$, $R_2$ and $R_3$ denote the radical of formula II

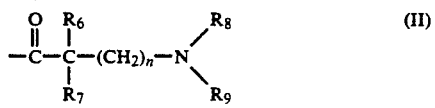

and the other or others hydrogen, where
$R_6$ and $R_7$ are identical or different and represent hydrogen, $(C_1-C_6)$-alkyl or an aryl radical,
n stands for 0 or an integer from 1 to 10, $R_8$ denotes hydrogen if $R_9$ represents hydrogen, unsubstituted or substituted $(C_1-C_6)$-alkyl, $(C_5-C_7)$-cycloalkyl, aryl-$(C_1-C_2)$-alkyl, aryl, a heterocyclic hydrocarbon wherein the heteroatoms may be oxygen, nitrogen or sulfur, optionally substituted amino, hydroxyl, acyl, di-$(C_1-C_6)$-alkylamino, carbonyl, $(C_1-C_6)$-alkoxycarbonyl, $(C_1-C_6)$-alkylcarbonyl-$(C_1-C_6)$-alkyl, or $R_8$ and $R_9$ have the same meaning and stand for optionally substituted $(C_1-C_6)$-alkyl, aryl, or aryl-$(C_1-C_2)$-alkyl, or $R_8$ denotes $(C_1-C_6)$-alkyl and $R_9$ represents substituted $(C_1-C_6)$-alkyl, $(C_5-C_7)$-cycloalkyl, aryl-$(C_1-C_6)$-alkyl or di-$(C_1-C_6)$-alkylamino-$(C_1-C_6)$-alkyl, or $R_8$ and $R_9$ together with the N-atom to which they are attached represent a heterocyclic hydrocarbon which in addition to the N-atom may contain one or more heteroatoms from the group comprising nitrogen, oxygen and sulfur and may be singly or multiply substituted by $(C_1-C_6)$-alkyl, aryl-$(C_1-C_6)$-alkyl, hydroxy-$(C_1-C_6)$-alkyl, aryl, hydroxyl or further heterocyclic hydrocarbons, or $R_1$, $R_2$ and/or $R_3$ denote

in which Z represents oxygen or sulfur, and A either represents the radical

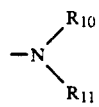

in which $R_{10}$ represents hydrogen or $(C_1-C_6)$-alkyl, and $R_{11}$ represents $(C_1-C_6)$-alkyl, $(C_3-C_7)$-cycloalkyl, aryl, aryl-$(C_1-C_6)$-alkyl, $(C_2-C_6)$-carbalkoxy or sulfonylaryl, or $R_{10}$ and $R_{11}$, together with the nitrogen atom to which they are bonded, form a heterocycle which may contain as further heteroatom oxygen, nitrogen or sulfur, or A represents the radial $-OR_{12}$ in which $R_{12}$ represents $(C_1-C_6)$-alkyl or halogeno-$(C_1-C_6)$-alkyl, or $R_1$ represents a tris-$(C_1-C_6)$-alkyl-silyl group, and $R_2$ and $R_3$ have the meanings given above, $R_4$ denotes ethyl, a vinyl group, —CHO,

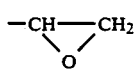

or —CH(OX)CH$_2$OX, where X is H or —C(O)-$(C_1-C_3)$-alkyl and $R_5$ denotes H, OH or O—$(C_1-C_3)$-alkyl and the pharmaceutically accpetable salts thereof.

Particularly preferred pharmaceutical compositions are those, wherein the compounds of group A) are selected from the group of compounds of formula I as described above, which are characterized by at least one of the following attributes:

R denotes H or OH, $R_1$-$R_3$ denote independently from each other H or

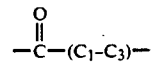

alkyl or either all three, two or one of the substituents $R_1$-$R_3$ denote the group of formula II, as described above, in which n is an integer from 0 to 5, and the other(s) denote H, $R_6$ and $R_7$ represent H or $R_6$ represents hydrogen and $R_7$ represents $(C_1-C_4)$-alkyl, $R_8$ represents $(C_1-C_{10})$-alkyl and $R_9$ represents cyclohexyl or $R_8$ and $R_9$ together with the N-atom to which they are attached represent the piperidino, morpholino, thiomorpholino, piperazino, imidazole, theophyllino or pyrrolidino radical, $R_4$ denotes vinyl or CHOHCH$_2$OH and $R_5$ denotes H.

Many from the compounds of group A) may form salts from organic or inorganic acids. Suitable examples of salts from organic or inorganic acids are hydrochloride, hydrobromide, sulfate, phosphate, acetate, oxalate, tartrate, citrate, maleate or fumarate.

The compounds of group B) for which Trequinsin (cf. IRCS Med. Sci. 1981, 9, 325; Life Sci., 1984, 31, 2037; Naunyn-Schmiedeberg's Arch. Pharmacol., 1982, 319, Suppl. R49) is an example, are explicitly described in b) Deutsche Offenlegungsschriften 27 20 085 and 28 01 289 and in the Indian patents 147 624, 149 432 and 149 457. Preferred compounds are described and exemplified in the patent applications cited under b). Further preferred compounds of group B) are characterized by the formula III

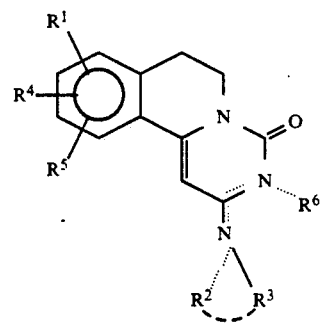

in which $R^1$, $R^4$ and $R^5$, which may be the same or different, stand for hydrogen, hydroxy, lower alkoxy, dialkylphosphinylalkoxy, acyloxy or halogen, two of the radicals $R^1$, $R^4$ or $R^5$, when in adjacent positions and taken together, may form a methylenedioxy or ethylenedioxy group, $R^2$ and $R^3$, which may be the same or different, stand for hydrogen, hydroxy, lower alkoxy, amino, alkylamino, dialkylamino, arylamino, amino or alkyl substituted by a 5- or 6-membered carbon ring containing up to 3 hetero atoms selected from the group of N, O and S; alkyl, cycloalkyl, hydroxyalkyl, alkoxyalkyl, dialkoxyalkyl, haloalkyl, dialkylaminoalkyl, aralkyl, acyl and optionally substituted aryl, aryl denoting an aromatic hydrocarbon radical having up to 10 carbon atoms;

$R^2$ represents a pair of electrons if $R^6$ stands for one of the radicals defined below and R² and R³ when taken together with the nitrogen atom to which they are bound may form an optionally substituted nitrogen heterocycle possibly containing a further nitrogen or oxygen atom, and R⁶ stands for hydrogen, alkyl, cycloalkyl, hydroxyalkyl, alkoxyalkyl, dialkoxyalkyl, haloalkyl, dialkylaminoalkyl, aralkyl, heterocyclically substituted alkyl, dialkylphosphinylalkyl, acyl and optionally substituted aryl or R⁶ represents a pair of electrones if R² represents one of the radicals defined above; and the acid addition salts and quaternary ammonium salts thereof.

In the case of at least one of the two radicals R² and R³ being hydrogen, the above definition of the pyrimido(6,1-a)isoquinolin-4-one derivatives also encompass the isomers of the following formula Ib, obtained by complete isomerization of compounds of formula Ia or being in equilibrium with the compounds of formula Ia.

suitable nitrogen-containing heterocyclic amino radical for R² or R³ is, for example, the N-morpholinoamino radical.

As alkyl radical for R², R³ or R⁶ there can be used those having at most 6 carbon atoms, for example methyl, ethyl, n-propyl, isopropyl, butyl, isobutyl, sec.-butyl or tert.butyl.

Suitable cycloalkyl radicals for R², R³ and R⁶ are those having at most 6 carbon atoms, for example cyclohexyl.

In the case of R², R³ or R⁶ being a substituted alkyl radical there may be used those having up to 6 carbon atoms and substituted by one or two hydroxy or ($C_1$-$C_3$)-alkoxy groups, halogen atoms, for example chlorine, amino or di-($C_1$-$C_4$)-alkyl-amino, dialkylphosphinylalkyl, for example dimethylphosphinylmethyl.

Examples of aralkyl radical for R², R³ and R⁶ are those having at most 8 carbon atoms, in which the aryl radical may be mono- or polysubstituted, especially

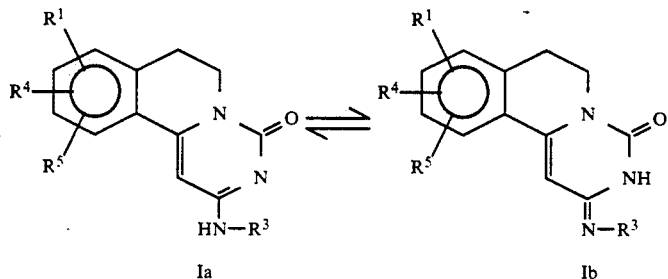

Ia        Ib

The definition of the pyrimido(6,1-a)isoquinolin-4-one derivatives also encompass the isomer of formula Ic

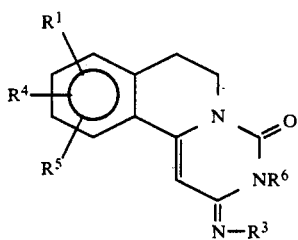

Ic in which R¹, R³, R⁴, R⁵ and R⁶ have the above meanings.

If R¹, R², R³, R⁴ and R⁵ stand for lower alkoxy groups, those having up to 3 carbon atoms are suitable.

Suitable acyloxy radicals for R¹, R⁴ or R⁵ are those in which the acyl group is linear or branched ($C_1$-$C_6$)-alkanoyl, for example acetyl, or aroyl, especially benzoyl in which the phenyl nucleus may be substituted one to three times by halogen, nitro, hydroxy, ($C_1$-$C_3$)-alkoxy and ($C_1$-$C_3$)-alkyl.

If R¹, R⁴ or R⁵ stand for halogen, chlorine is preferred. Suitable dialkylphosphinylalkoxy radicals for R¹, R⁴ or R⁵ are those in which the alkyl and alkoxy groups carry at most 3 carbon atoms, for example dimethylphosphinylmethoxy.

Especially suitable alkylamino or dialkylamino radicals for R² or R³ are those in which the alkyl groups have at most 3 carbon atoms, for example methylamino or dimethylamino.

Suitable arylamino radicals for R² or R³ are phenylamino radicals in which the phenyl residue may be substituted one or several times by halogen, for example chlorine, ($C_1$-$C_3$)-alkyl, for example methyl, or nitro. A substituted one, two, or three times by the substituents defined above for R¹.

Suitable heterocyclic alkyl radicals for R², R³ and R⁶ are, for example, furfuryl and tetrahydrofurfuryl.

Suitable examples of aryl radicals for R², R³ and R⁶ are phenyl radicals optionally substituted one or several times, preferably one, two or three times by halogen, for example fluorine, chlorine and bromine, ($C_1$-$C_3$)-alkyl and ($C_1$-$C_3$)-alkoxy, for example methyl, ethyl, methoxy and ethoxy, haloalkyl, for example trifluoromethyl, amino or hydroxy, in the latter the hydrogen atoms possibly being replaced by an alkali metal, for example sodium.

Suitable nitrogen-containing heterocyclic radicals are, for example, pyrrolidino, piperidino, morpholino, and piperazino, optionally substituted by alkyl, alkoxycarbonyl, aryl or a nitrogen heterocycle, the terms alkyl, alkoxy, aryl and nitrogen heterocycle having the above meaning.

Examples of suitable acyl radicals for R², R³ and R⁶ are linear or branched ($C_1$-$C_6$)-alkanoyl, such as acetyl, or aroyl, such as benzoyl, wherein the phenyl residue may be substituted one or several times by the substituents defined above for R², R³ and R⁶ when they represent an aryl radical.

As salts of the pyrimido(6,1-a)isoquinolin-4-one derivatives of the invention there are mentioned by way of example those of inorganic or organic acids, for example the hydrochlorides, hydrobromides, sulfates, phosphates, acetates, oxalates, tartrates, citrates, maleates or fumarates.

Suitable quaternary ammonium salts of the pyrimido(6,1-a)-isoquinolin-4-one derivatives of the invention are, for example, the salts derived from alkyl halides, such as methiodides.

Preferred substituents are: alkoxy for $R^1$ and $R^4$, hydrogen for $R^5$, ($C_1-C_6$)-alkyl or phenyl optionally substituted one to three times as defined above for $R^2$, hydrogen, ($C_1-C_6$)-alkyl, cycloalkyl, substituted alkyl, aralkyl, heterocyclic alkyl, substituted aryl and ($C_1-C_6$)-alkanoyl for $R^3$ and $R^6$.

Particularly preferred compounds are:

9,10-dimethoxy-2-tert.-butylamino-6,7-dihydro-4H-pyrimido-(6,1-a)isoquinoline-4-one hydrochloride, 9,10-dimethoxy-2-(2,4,6-trimethylanilino)-6,7-dihydro-4H-pyrimido(6,1-a)-isoquinolin-4-one hydrochloride dihydrate, 9,10-dimethoxy-3-methyl-2-mesitylimino-2,3,6,7-tetrahydro-4H-pyrimido(6,1-a)isoquinolin-4-one hydrochloride, 9,10-dimethoxy-2-(N-methyl-2,4,6-trimethylanilino)-6,7-dihydro-4H-pyrimido(6,1-a)isoquinolin-4-one hydrochloride, 9,10-dimethoxy-3-isopropyl-2-mesitylimino-2,3,6,7-tetrahydro-4H-pyrimido(6,1-a)isoquinolin-4-one hydrochloride, 9,10-dimethoxy-2-(N-isopropyl-2,4,6-trimethylanilino)-6,7-dihydro-4H-pyrimido(6,1-a)isoquinolin-4-one hydrochloride, 9,10-dimethoxy-3-ethyl-2-mesitylimino-2,3,6,7-tetrahydro-4H-pyrimido(6,1-a)isoquinolin-4-one hydrochloride, 9,10-dimethoxy-2-(N-ethyl-2,4,6-trimethylanilino)-6,7-dihydro-4H-pyrimido(6,1-a)isoquinolin-4-one hydrochloride, 9,10-dimethoxy-3-acetyl-2-mesitylimino-2,3,6,7-tetrahydro-4H-pyrimido(6,1-a)isoquinolin-4-one and 9,10-dimethoxy-2-(N-acetyl-2,4,6-trimethylanilino)-6,7-dihydro-4H-pyrimido(6,1-a)isoquinolin-4-one.

The production of the compounds of groups A) and B) is explicitly described in the patents and patent applications cited above under a) and b).

A pharmaceutical composition with extraordinary activity contains 7β-acetoxy-8,13-epoxy-1α,6β,9α-trihydroxy-labd-14-en-11-one and 9,10-dimethoxy-2-mesitylimino-3-methyl-2,3,6,7-tetrahydro-4H-pyrimido(6,1-a)isoquinolin-4-one hydrochloride.

Detailed investigations have shown that the combined topical administration of at least one compound of group A) and at least one compound of group B) results in an activity on hair growth which is far in excess of that which would result when said compounds are used singly; thus, said combinations show a clear synergistic effect. An important advantage of the pharmaceutical compositions according to the instant invention is the fact that the compounds of group A) and group B) have an influence on hair growth through different mechanisms.

The pharmaceutical compositions according to the instant invention can be administered to any mammals, however, they have a special importance for the human being.

For the increase of hair growth and for the treatment of alopecia (e.g. alopecia areata, alopecia totalis or androgenetic alopecia) a combination of one or more compounds of group A) and one or more compounds of group B) is administered, preferably topically, optionally together with suitable carriers and/or excipients. Examples of application forms which may be mentioned are solutions, suspensions, emulsions, pastes, ointments, soaps, jellies, creams, lotions, dusting powders, surfactant containing cleansing products, oils, sprays, aerosols and the like.

Any desired carriers and/or excipients are added to the pharmaceutical composition. Excipients which are to be preferred are derived from the group of preservatives, antioxidants, stabilizers, solubilizers, vitamins, colorants and odor improvers.

Ointments, pastes, creams and jellies can, besides the active substance(s), contain the customary excipients, for example animal and vegetable fats, waxes, paraffins, starch, tragacanth, cellulose derivatives, polyethylene glycols, silicones, bentonite, silica, talc and zinc oxide, or mixtures of these substances.

Dusting powders and sprays can, besides the active substance(s), contain the customary excipients, for example lactose, talc silica, aluminum hydroxide, calcium silicate and polyamide powder, or mixtures of these substances. Sprays can additionally contain the customary propellants, for example chlorofluorohydrocarbons, propane/butane or dimethyl ether.

Solutions and emulsions can, besides the active substance(s), contain the customary excipients such as solvents, solubilizers and emulsifiers, for example water, ethanol, isopropanol, ethyl carbonate, ethyl acetate, benzyl alcohol, benzyl benzoate, propylen glycol, dimethylacetamide, 1,3-butylglycol, oils, especially cottonseed oil, peanut oil, corn oil, olive oil, castor oil and sesame oil, glycerol fatty acid esters, polyethylene glycols and fatty acid esters of sorbitan, or mixtures of these substances.

Suspensions can, besides the active substance(s), contain the customary excipients such as liquid diluents, for example water, ethanol or propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

Soaps can, besides the active substance(s), contain the customary excipients such as, for example, alkali metal salts or fatty acids, salts of fatty acid hemiesters, fatty acid protein hydrolyzates, isethionates, lanolin, fatty alcohols, vegetable oils, plant extracts, glycerol, sugar, or mixtures of these substances.

Surfactant-containing cleansing products can, besides the active substance(s), contain the customary excipients such as, for example, salts of fatty alcohol sulfates, fatty alcohol ether sulfates, sulfosuccinic hemiesters, fatty acid protein hydrolyzates, isethionates, imidazolinium derivatives, methyllaurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Oils can, besides the active substance(s), contain the customary excipients such as, for example, synthetic oils such as fatty acid esters, fatty alcohols, silicone oils, neutral oils such as vegetable oils, and oily plant extracts, liquid paraffins, lanolin oil, or mixtures of these substances.

A physiologically effective amount of a pharmacologically acceptable composition is applied to the scalp as often as required. A preferred concentration of the compounds of group A) and the compounds of group B) in combination, when administered as topical solution to the scalp is in the range of 0.1% to 5%.

The particularly preferred range of concentration is 0.5-3%. The ratio of the compounds of group A) to the compounds of group B) may vary from 1:99 to 99:1.

The preferred solvents for solutions are such as water, ethanol, propylene glycol, dimethylacetamide, used singly or in combination in appropriate proportion to keep the active ingredients in solution. The number of administrations per day to the deltoid areas is dependent on the concentration of the active ingredient(s) administered. Application of the solutions may be made by way of contact occlusion to the deltoid areas. Occlusion of the solution may be obtained by any conventional means such as bandages, plastic coverings, shower caps, swimming caps etc.

The following examples illustrate the invention but are not to be construed as limiting.

EXAMPLE 1

One thousand ml of an aqueous solution containing 2% 9,10-dimethoxy-2-mesitylimino-3-methyl-2,3,6,7-tetrahydro-4H-pyrimido(6,1-a)isoquinolin-4-one hydrochloride and 2% 7$\beta$-acetoxy-8,13-epoxy-1$\alpha$,6$\beta$,9$\alpha$-trihydroxy-labd-14-en-11-one is prepared from the following types and amount of ingredients.

| | |
|---|---|
| 9,10-Dimethoxy-2-mesitylimino-3-methyl-2,3,6,7-tetrahydro-4H-pyrimido(6,1-a)-isoquinolin-4-one hydrochloride | 20 g |
| 7$\beta$-Acetoxy-8,13-epoxy-1$\alpha$,6$\beta$,9$\alpha$-trihydroxy-labd-14-en-11-one | 20 g |
| Propylene glycol | 250 g |
| Polyethylene glycol | 400 g |
| Ethyl alcohol | 300 g |
| Dionised water q.s. ad | 1000 ml |

The ingredients 9,10-dimethoxy-2-mesitylimino-3-methyl-2,3,6,7-tetrahydro-4H-pyrimido(6,1-a)isoquinolin-4-one hydrochloride and 7$\beta$-acetoxy-8,13-epoxy-1$\alpha$,6$\beta$,9$\alpha$-trihydroxy-labd-14-en-11-one are dissolved separately into propylene glycol and polyethylene glycol maintaining the temperature of 35°–45° C. The solutions are then cooled to room temperature and mixed under stirring and further diluted with ethanol first and then with water to make the volume of the solution to 1000 ml. The resulting solution is sterilised by filtration. The solution is then filled aseptically into sterile containers.

EXAMPLE 2

A solution containing 1% 9,10-dimethoxy-2-mesitylimino-3-methyl-2,3,6,7-tetrahydro-4H-pyrimido(6,1-a)isoquinolin-4-one hydrochloride and 1% 7$\beta$-acetoxy-8,13-epoxy-1$\alpha$,6$\beta$,9$\alpha$-trihydroxy-labd-14-en-11-one is prepared from the following amount of ingredients

| | |
|---|---|
| 9,10-Dimethoxy-2-mesitylimino-3-methyl-2,3,6,7-tetrahydro-4H-pyrimido(6,1-a)-isoquinolin-4-one hydrochloride (Trequinsin) | 1 g |
| 7$\beta$-Acetoxy-8,13-epoxy-1$\alpha$,6$\beta$,9$\alpha$-trihydroxy-labd-14-en-11-one (Forskolin) | 1 g |
| Propylene glycol | 40 ml |
| Ethyl alcohol q.s. ad | 100 ml |

The ingredients 9,10-dimethoxy-2-mesitylimino-3-methyl-2,3,6,7-tetrahydro-4H-pyrimido(6,1-a)isoquinolin-4-one hydrochloride and 7$\beta$-acetoxy-8,13-epoxy-1$\alpha$,6$\beta$,9$\alpha$-trihydroxy-labd-14-en-11-one are dissolved in propylene glycol at room temperature under stirring and further diluted with ethanol to make the volume of the solution to 100 ml. The resulting solution is sterilised by filtration. The solution is then filled aseptically into sterile containers.

The solutions were also prepared similarly using tetraglycol in place of a mixture of polyethylene glycol and propylene glycol in the above example.

The solutions so prepared can be used in the topical application for treatment of male pattern baldness by application to the affected area of the scalp daily.

Detection of Hair Growth-Promoting Effect of Forskolin + Trequisin.

Male and female rabbits having a weight of 500–700 g and an age of 5–6 weeks were used for the experiments. The animals were kept with the mother during the entire experiment.

The rear part of the experimental animals was shaved in four sites (two on each side) using electric hair clippers. Each animal had 4 shaved sites of 3 cm$^2$ each. 18 hours after shaving, 0.2 ml of test solution (see Example 2) and also solvent as a blank sample were placed on each shaved site and massaged in for about 60 sec. The application was repeated daily and at the end of each week in each case 10 hairs were pulled out from each site and their length was determined.

Solution of a mixture of Trequisin and Forskolin having a content of 1% of each active compound was used.

Results obtained are shown in Table 1.

TABLE 1

Hair growth in mm in rabbits under the influence of treatment with a solution containing Trequisin and Forskolin

| Treatment period in weeks | Solvent | Solution containing Trequisin + Forskolin |
|---|---|---|
| 1 | 9.88 ± 0.38 | 10.32 ± 0.49 |
| 4 | 13.78 ± 0.91 | 15.38 ± 0.91 |
| 5 | 19.10 ± 0.88 | 22.26 ± 0.89 |

We claim:

1. A method for promoting hair growth and for arresting hair loss which comprises topically administering an effective amount of a pharmaceutical composition containing at least one compound of group A) consisting of labdane diterpenoid derivatives and at least one compound of group B) consisting of pyrimido(6,1-a)isoquinoline-4-one derivatives.

2. A method for treating androgenic alopecia, alopecia areata, and alopecia totalis which comprises topically administering an effective amount of a pharmaceutical composition containing at least one compound of group A) consisting of labdane diterpenoid derivaties and at least one compound of group B) consisting of pyrimido(6,1-a)isoquinolin-4-one derivatives to the affected area.

* * * * *